(12) United States Patent
Norton

(10) Patent No.: US 10,166,150 B2
(45) Date of Patent: Jan. 1, 2019

(54) THERAPEUTIC COMPRESSION DEVICE AND METHOD

(75) Inventor: Steven Norton, Fair Haven, NJ (US)

(73) Assignee: Norton Salas Group, Inc., Matawan, NJ (US)

( * ) Notice: Subject to any disclaimer, the term of this patent is extended or adjusted under 35 U.S.C. 154(b) by 1064 days.

(21) Appl. No.: 13/193,225

(22) Filed: Jul. 28, 2011

(65) Prior Publication Data
US 2013/0030335 A1 Jan. 31, 2013

(51) Int. Cl.
*A61H 7/00* (2006.01)
*A61F 13/10* (2006.01)
*A61F 13/08* (2006.01)

(52) U.S. Cl.
CPC ............ *A61F 13/08* (2013.01); *A61F 13/104* (2013.01); *A61H 7/001* (2013.01); *A61H 2201/1635* (2013.01); *A61H 2205/065* (2013.01)

(58) Field of Classification Search
CPC ...... A61F 13/08; A61F 13/085; A61F 13/104; A61H 2011/005; A61H 2205/065; A61H 2201/1635; A61H 2201/1645; A61H 7/001
USPC .... 601/1, 134–136, 148, 151; 602/7, 12, 21, 602/27, 78; 36/50.1, 50.5
See application file for complete search history.

(56) References Cited

U.S. PATENT DOCUMENTS

| | | | |
|---|---|---|---|
| 4,676,233 A | 6/1987 | Scheinberg | |
| 5,152,302 A | 10/1992 | Fareed | |
| 6,024,712 A * | 2/2000 | Iglesias | A61F 5/0111 602/27 |
| 6,077,241 A * | 6/2000 | Fareed | A61F 13/00 2/16 |
| 6,526,592 B1 | 3/2003 | Best | |
| 6,785,909 B1 | 9/2004 | Li | |
| 6,991,612 B2 | 1/2006 | Scheinberg et al. | |
| 7,135,005 B2 | 11/2006 | Kania | |
| D617,464 S * | 6/2010 | Weaver, II | D24/190 |
| 2005/0066412 A1 | 3/2005 | Morrow | |
| 2006/0135902 A1 | 6/2006 | Ingimundarson et al. | |
| 2006/0156517 A1* | 7/2006 | Hammerslag | A43B 5/16 24/68 SK |
| 2006/0264792 A1* | 11/2006 | Bonn | A61F 5/0118 602/21 |
| 2007/0100266 A1* | 5/2007 | Hargrave et al. | 602/21 |

(Continued)

FOREIGN PATENT DOCUMENTS

WO WO 2010099130 A1 * 9/2010

*Primary Examiner* — Colin W Stuart
*Assistant Examiner* — Douglas Sul
(74) *Attorney, Agent, or Firm* — Thomas L. Adams

(57) ABSTRACT

A compression device can treat edema with a number of curved shells, each having an internal pad. A ligature network employing tensioners is routed across the shells for compressing them. Tensioners on at least some of the shells can separately adjust tension in different portions of the ligature network. The ligature network is (a) releasably mounted on the shells, and (b) repositionable to allow spatial adjustment of compression forces produced by the compression device. By adjusting the routing of the ligature network across the shells, tailored compression forces are provided. With a body part embraced by the padded shells, tension is separately adjusted in different portions of the ligature network to provide different compression forces at spaced positions along the plurality of padded shells.

38 Claims, 4 Drawing Sheets

(56) References Cited

U.S. PATENT DOCUMENTS

| | | | |
|---|---|---|---|
| 2008/0083135 A1* | 4/2008 | Hammerslag et al. | 36/50.5 |
| 2008/0228117 A1 | 9/2008 | Fareed | |
| 2010/0056973 A1* | 3/2010 | Farrow et al. | 602/63 |
| 2010/0168630 A1* | 7/2010 | Cropper | A61F 5/024 602/19 |
| 2012/0004587 A1* | 1/2012 | Nickel | A61F 5/0118 602/21 |
| 2012/0010547 A1* | 1/2012 | Hinds | A61F 5/013 602/21 |
| 2012/0029404 A1* | 2/2012 | Weaver et al. | 602/27 |
| 2012/0101417 A1* | 4/2012 | Joseph | 602/5 |
| 2014/0121579 A1* | 5/2014 | Hinds | A61F 5/013 602/21 |

\* cited by examiner

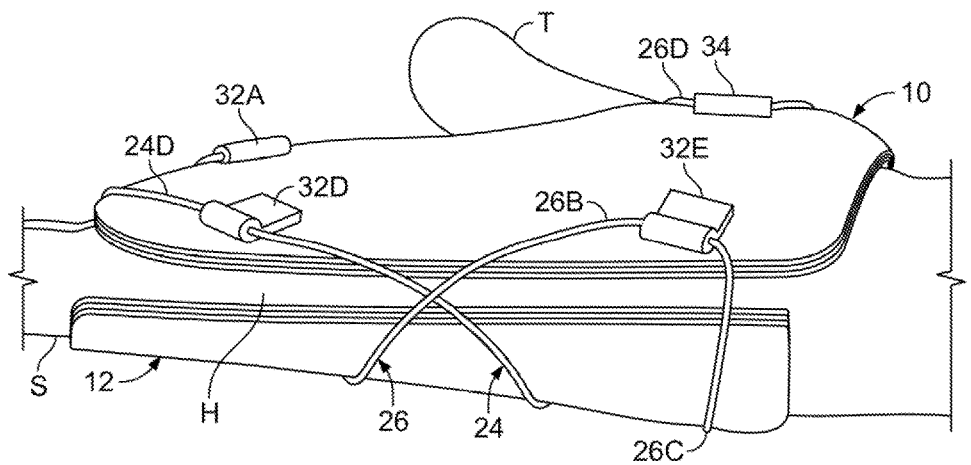
FIG. 3
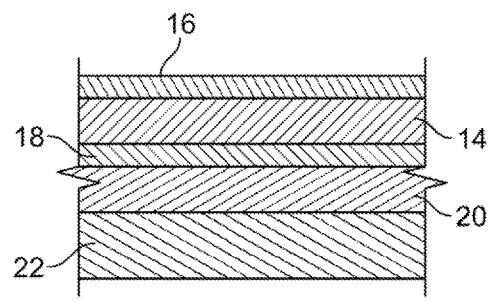
FIG. 4
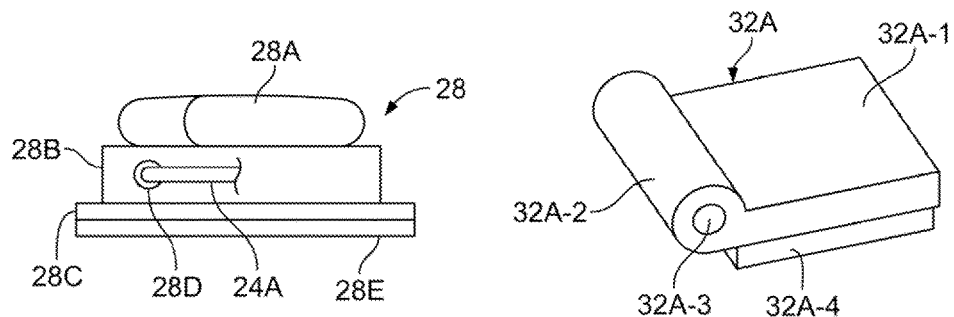
FIG. 5
FIG. 6

THERAPEUTIC COMPRESSION DEVICE AND METHOD

BACKGROUND OF THE INVENTION

1. Field of the Invention

The present invention relates to devices and method for treating a patient with compression, and in particular, to techniques employing separate shells.

2. Description of Related Art Edema is a medical condition that requires careful treatment. Lymphedema, a type of edema, is a swelling of a body part, often the result of the abnormal accumulation in the affected area of protein-rich edema fluid (primarily lymph fluids). Lymphedema is classified as either primary or secondary. Primary lymphedema is the result of lymphatic dysplasia. It may be present at birth but more often develops later in life without obvious cause. Secondary lymphedema is much more common and is the result of surgery or is a side effect of radiation therapy for cancer. Secondary forms may also occur after injury, scarring, trauma, or infection of the lymphatic system. Lymphedema treatment options offered in the United States include surgery, medication, pneumatic compression pump therapy, Manual Lymph Drainage (MLD), and Complete Decongestive Therapy (CDT).

Surgery and medication have their place, but their success is not guaranteed and comes with risks. The pneumatic compression pump is a mechanical device that "milks" the lymph fluid out of the swollen extremity. The problems with pneumatic pumps are numerous and any results achieved are usually very temporary.

Lymphedema physical therapy treatment would not be possible without compression therapy employing bandages and elastic compression garments. Elastic compression garments are easily used and sold under the trade names: Solaris, JoviPak, CircAid, Biacare, and Reid Sleeve. Another compression therapy involves bandaging with short stretch bandages and is a highly skilled procedure designed to take advantage of natural pumping pressures.

Lymph is propelled through the various lymph vessels by muscular activity, breathing, etc. Bandaging/garments improve the efficiency of the muscle and joint pump and also prevents the re-accumulation of evacuated lymph fluid. These techniques will also break up deposits of accumulated scar and connective tissue.

The nature of compression varies greatly when a comparison is made between short stretch bandages and elastic compression garments. Both are necessary complements to a program of Complete Decongestive Therapy (CDT) when utilized by competent and well-trained therapists. The distinction lies in the working and resting forces generated by these two forms of compression. Elastic compression garments are designed to provide a pressure gradient favoring proximal fluid flow and are comfortable and convenient. However, they tend to produce constant resting pressure without enhanced working pressure. Short stretch compression bandages supports a limb without constant "squeezing" (i.e. will exhibit low resting pressure), but when a limb is exercised produces relatively high working pressure.

No effective homecare device exists to maintain/reduce lymphedema/edema consistent with the principles of CDT (Complete Decongestive Therapy). Therefore, patients are saddled with the responsibility of life-long lymphedema control, but the task is arduous, tedious and time consuming. When self-applied compression is performed with less than sufficient skill, it can also be painful, counter-therapeutic or even damage the limbs' health.

Aftermarket compression products have tried alternative solutions to replace multilayered compression bandages. Treatment at joints is most problematical for these products. Even at the limb segments (between joints) the solutions offered utilize unsatisfactory materials and tensioning techniques to generate pressure. As a result these products lack continuous working pressure (cast-like containment) longitudinally as well as structure to prevent buckling and bulging of tissues.

See also U.S. Pat. Nos. 4,676,233; 5,152,302; 6,526,592; 6,785,905; 7,135,005; and 6,991,612; as well as US Patent Application Publication Nos. 2005/0066412; 2006/0135902; and 2008/0228117.

SUMMARY OF THE INVENTION

In accordance with the illustrative embodiments demonstrating features and advantages of the present invention, there is provided a compression device for treating edema. The device includes a plurality of curved shells, each having an internal pad. The device also includes a ligature network routed across the plurality of shells. The network includes a plurality of tensioners. The tensioners are mounted on at least some of the plurality of shells and are operable to separately adjust tension in different portions of the ligature network.

In accordance with another aspect of the invention, a compression device is provided for treating edema. The device includes a plurality of curved shells, each having an internal pad. The device also includes a ligature network routed across the shells. The ligature network includes a plurality of tensioners mounted on at least some of said plurality of shells. At least at least a portion of the ligature network is releasably mounted and repositionable on the shells to allow spatial adjustment of compression forces produced by said compression device In accordance with yet another aspect of the invention, a method is provided for treating edema with a ligature network and a plurality of padded shells. The method includes the step of routing the ligature network across the plurality of shells. Also, with a body part embraced by the padded shells, the method performs the step of separately adjusting tension in different portions of the ligature network to affect the balance of compression forces at spaced positions along the plurality of padded shells.

In accordance with still yet another aspect of the invention, a method is provided for treating edema with a ligature network and a plurality of padded shells. The method includes the step of adjusting routing of the ligature network across the plurality of shells to provide tailored compression forces at spaced positions along the plurality of padded shells. Also, with a body part embraced by the padded shells, the method performs the step of adjusting tension in the ligature network to adjust compression forces along the plurality of padded shells.

By employing devices and methods of the foregoing type an improved technique is achieved for treating edema. For example, lymphedema limb areas need not be immobilized and the present device does not function as a cast or an immobilizer. Areas of joint articulation can sustain movement without abrasion or discomfort. The natural muscle and joint pumps will be allowed to activate a natural fluid pumping effect. Allowing movement within a compression device tends to reverse lymphostatic fibrosis.

A disclosed embodiment is presented for treating the hand, although treatment of other body parts is described.

The embodiment for treating the hand employs a pair of padded shells, one placed on the palm and one on the dorsum.

These padded shells each have a heat-treatable, plastic panel that is relatively stiff, so that the shells can apply transaxial pressure without squeezing the hand laterally. This arrangement cancels out high lateral pressures, and accentuates high dorsal and palmar pressures.

These panels are fashioned to accommodate the specific body part being treated. For example, an outline of a hand may be applied to plastic panels and used to trim them accordingly, although the final panel outline need not follow the exact outline of the hand. Typically, the panel will be notched to allow articulation of the thumb.

The panels may be heated to soften and bend them into a curve that accommodates the curves of the hand or other body part under treatment.

Lymphedema is a staged condition according to disease severity (stages 1, 2, 3). As such it requires modifications in the approach according to the quantity of swelling and tissue integrity. The above noted shells apply the external force, but inner-padding materials must be tailored to modify the force according to the disease severity, desired gradient of pressure, limb girth and abnormal contours if any.

With this in mind, the inside of the disclosed panels will be fitted with pads; for example, multiple layers of foam material. In one case the layer on the plastic panel is a closed cell foam that readily accommodates transaxial force, while the layer contacting skin tissue is an open cell foam that conforms more closely to the curves of the hand and increases comfort. In some cases one or more of the layers will not be one continuous piece, but will be formed from multiple disjoint segments that are fashioned to tailor the pressure being applied to the body part under treatment.

Proper treatment requires that skin integrity be preserved to combat any localized immune deficiency. To address this requirement the shells' pads ought to be hypoallergenic, customized to the patient, and hygienic. Moreover, any inner layer in contact with the skin should be exchanged regularly.

Lymphedema treatment requires that a gradient of pressure be exerted regardless of the contour of the swollen limb. Pressure applied to hypothetical conical shapes will respond according to the "law of Laplace" (P=Tc/R), however swollen limbs are not always conical. To address this anatomical requirement "zones" of pressure are created and padding modified suitably to direct fluid from distal areas towards proximal areas. Limbs that have received treatment in the clinic (e.g., with CDT) become more normally shaped (from columnar to conical again) and readily responsive to the above compression device.

In order to achieve an appropriate pressure, a disclosed embodiment employs a ligature network that is formed from a number of cords that are routed across the padded shells. Specifically, these cords are routed through guides strategically placed at various locations on the opposing shells. A disclosed network has two circuits that are independently tightened by two tensioners. The disclosed tensioners are cord winders placed in strategic locations on one or more of the shells.

In this embodiment, the guides and winders are easily repositioned to modify the routing of the cords in the ligature network. Specifically, the guides and winders are attached to the outside of the shells by hook and loop fasteners.

Devices of this type may be used as an adjunct to, or a follow-up after, professional therapy. Also, after the initial fitting of the device, a user will be able to readily remove the device and later place it back on the body part under treatment without the need for professional assistance. In addition, since the tension in the ligature network is readily adjusted, a user can easily adjust tension throughout the day as needed.

Devices according to the foregoing principles can achieve high working pressure, and low resting pressure throughout. Such devices are adaptable to the edema reduction process by allowing movement, and normal activity. In the disclosed embodiment, tension is easily adjusted so a user is able to regularly conduct subtle re-tensioning.

BRIEF DESCRIPTION OF THE DRAWINGS

The above brief description as well as other objects, features and advantages of the present invention will be more fully appreciated by reference to the following detailed description of illustrative embodiments in accordance with the present invention when taken in conjunction with the accompanying drawings, wherein:

FIG. 3 is a side view of the compression device of FIGS. 1 and 2;

FIG. 4 is a sectional view of a fragment of one of the padded shells of the device of FIGS. 1 and 2;

FIG. 5 is a side view of one of the tensioners of FIG. 1;

FIG. 6 is a perspective view of one of the guides of FIGS. 1 and 2;

DETAILED DESCRIPTION

Figures 1, 2:
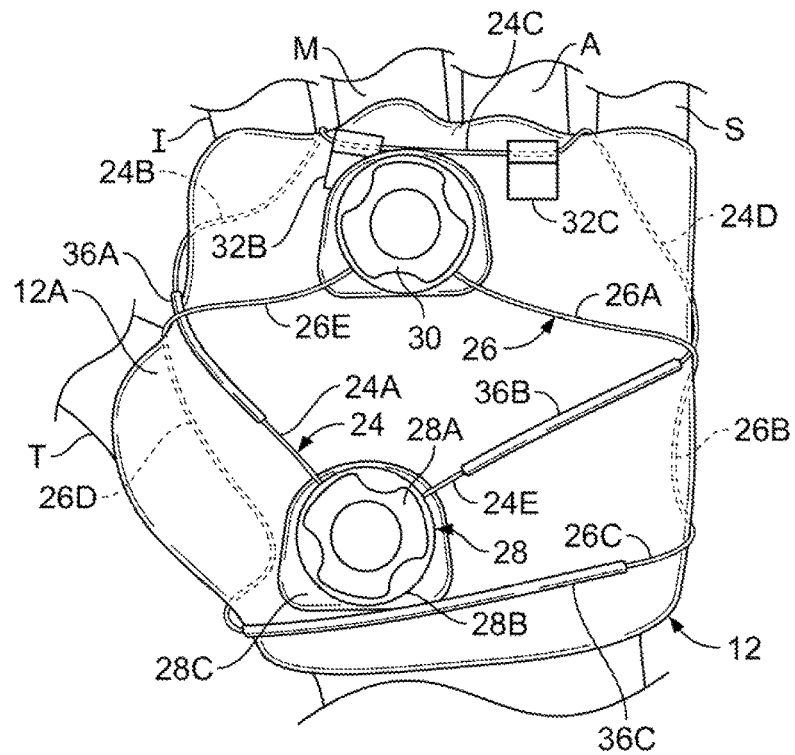
FIG. 1 is a top view of a compression device in accordance with principles of the present invention.
FIG. 2 is a bottom view of the compression device of FIG. 1.

Referring to FIGS. 1-7, the illustrated compression device has a palmar shell 10 and a dorsal shell 12, each designed for right hand H. Each of the shells 10 and 12 have a heat-deformable plastic panel 14 (FIG. 4). Various types of thermoplastics will operate satisfactorily as a panel, and the Aquaplast® moldable sheets from Patterson Medical (1.6 to 3.2 mm thick, perforated) will operate satisfactorily. Panel 14 ought to be relatively stiff in order to transmit compression forces normal to its surface. In this embodiment the opposite faces of panel 14 have a coterminous covering 16 and 18 in the form of a sheet of hook and loop material (loop material prominent) on a breathable plastic substrate.

FIG. 1 shows the outline of padded shell 12, it being understood that the right and left edges are rolled about 45°, except at the extension 12A provided for thumb T. One can establish the outline of shell 12 by tracing the outline of the hand (hand H of FIG. 2) on panel 14 and trimming appropriately. The trimmed panel 14 will have additional material for the rolling of the right and left panel edges and will make accommodations for the extended thumb region 12A.

Thereafter, panel 14 can be heated by, for example, immersion in hot water. When heated, the right and left edges of panel 14 can be rolled as noted above, while the central region can be given an appropriate curve to accommodate the natural curves of hand H. The outline and curvature of panel 14 may be refined based on the judgment and experience gathered by a properly trained therapist. Also, after an initial shaping, panel 14 can be placed against hand H to determine what areas need correction before possibly trimming and reshaping the panel again.

FIG. 2 shows the outline of padded shell 10 with the right and left edges again rolled about 45°, except in the vicinity of notch 10A provided for thumb T. Panel 14 of shell 10 can be trimmed and curved in a manner similar to that described in connection with shell 12.

The faces of panels 14 of shells 10 and 12 that face the skin are fitted with an internal pad, shown in FIG. 4 as a pair of resilient layers 20 and 22. Layers 20 and 22 will be trimmed to be coterminous with their associated shells 10 and 12.

Distal layer 20 may be formed of a closed cell foam material of the type typically used in compression therapy for lymphedema patients. Such lymphedema grade foams are available under the trade names Jobst Foam or Komprex Foam. Foams of this type are resilient but still tend to transmit compression forces substantially perpendicular to shell panel 14. Layer 20 will be secured onto hook and loop material 18, using, if necessary, an additional hook and loop sheet (hooks prominent).

It is desirable that proximal layer 22 be more compliant than layer 20 to add to the wearer's comfort. Also, a softer material will tend to feather the compression forces near the edges of the device, thereby avoiding the tendency to apply undesired lateral compression. Open cell foam material has been found satisfactory for this purpose, although other types of resilient materials can be used as well. An acceptable open cell foam material is available from Canal Rubber Supply Co. of New York (light to medium density).

In this embodiment layer 22 is ½ inch thick (1.3 cm). In other embodiments the layer thickness may be varied, although typically remaining within a range of ¼ to ¾ inch (0.6 to 1.9 cm) thick, with the thickness chosen to accommodate the needs of the patient.

Padded shells 10 and 12 are pressed together with a ligature network employing nylon cords arranged in a pair of circuits 24 and 26. Circuit 24 terminates at network tensioner 28, while circuit 26 terminates at network tensioner 30. In this embodiment tensioners 28 and 30 are identical, but need not be so. Circuit 24 has cord segment 24A running atop shell 12 through plastic tube 36A, which tube is designed to decrease cord friction. Cord segment 24A traverses the edge of shell 12 and crosses over to run atop shell 10, as shown by cord segment 24B.

Cord segment 24B is threaded through network guide 32A, which is releasably secured atop shell 10. Guide 32A is shown in FIG. 6 as a slab 32A-1 supporting sleeve 32A-2, which has through bore 32A-3 for receiving previously mentioned cord segment 24B. A sheet of hook and loop fastening material 32A-4 glued on the underside of slab 32A-1 is designed to releasably attach guide 32A to mating sheet 16 (FIG. 4) on shell 10. Guide 32A is identical to guides 32B, 32C, 32D and 32E shown in FIGS. 1 and 2 (these guides sometimes being referred to as annular implements).

Cord segment 24B traverses the edge of shell 10 and passes between forefinger I and middle finger M before running atop shell 12, as shown by cord segment 24C. Cord segment 24C is threaded through guides 32B and 32C, which are mounted atop shell 12. Cord segment 24B traverses the edge of shell 12 and passes between ring finger A and pinky finger S before running atop shell 10, as shown by cord segment 24D. Cord segment 24D is threaded through guide 32D, which is releasably secured atop shell 10. Cord segment 24D traverses the edge of shell 10 to run atop shell 12, as shown by cord segment 24E. Cord segment 24E passes through friction reducing tube 36B.

Referring now to circuit 26, cord segment 26A runs atop shell 12 and traverses the edge of shell 12 before running atop shell 10 as shown by cord segment 26B. Cord segment 26B is threaded through guide 32E, which is releasably secured atop shell 10. Cord segment 26B traverses the edge of shell 10 before running atop shell 12, as shown by cord segment 26C, which passes through friction reducing tube 36C. Cord segment 26C traverses the edge of shell 12 before running atop shell 10, as shown by cord segment 26D. Cord segment 26D runs through a channel in network guide 34, which is releasably secured atop shell 10.

Figure 7:
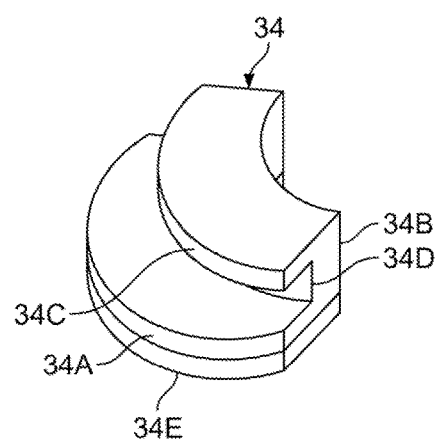
FIG. 7 is a perspective view of the curved guide of FIG. 2.

In FIG. 7 guide 34 is shown with a platform 34A having a curved outside edge (approximately a quarter circle curve) and an inside edge leading to a curved wall 34B (approximately a quarter circle curve). A similarly curved shelf 34C projecting from atop wall 34B forms a curved channel 34D to guide previously mentioned cord segment 26D. Hook and loop fastener 34E glued on the underside of platform 34A will releasably attach guide 34 to hook and loop fastening material 16 atop shell 10.

Tensioner 28 is shown in FIG. 5 having a dial 28A rotatably mounted on body 28B, which sits atop base 28C. Cord segment 24A is shown passing through hole 28D in body 28B. It will be appreciated that cord segment 24E passes through another hole (not shown) on the other side of body 28B. Tensioner 28 operates as a manually operable winder. Specifically, dial 28A can be rotated clockwise (counterclockwise) to wind (unwind) cord segments 24A relative to a reel (not shown) inside winder body 28B. Cord segment 24E will not be wound although winding may be implemented in other embodiments. Winders of this type can be obtained from Boa Technology, Inc. of Steamboat Springs, Colo.

A sheet of hook and loop material 28E is glued to the underside of winder base 28C to act as a fastening device that will releasably attach the winder 28 by mating to hook and loop material 16 atop shell 12 (FIG. 1).

Figure 8:
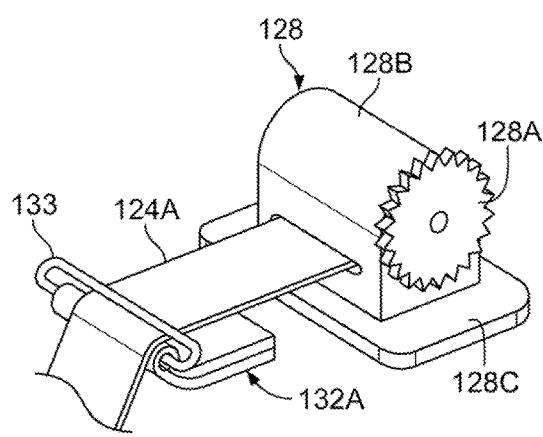
FIG. 8 is a fragmentary, perspective view of a tensioner in a ligature network that is an alternate to that shown in FIGS. 1 and 2.

Referring to FIG. 8, a different type of manually operable winder (tensioner) is illustrated. Components corresponding to those previously described in connection with FIG. 5 have the same reference numeral but increased by 100. The winder 128 has mounted atop base 128C a body 128B containing a winding reel (not shown) that is driven by dial 128A. Rotation of dial 128A will wind or unwind band 124A, which will be part of a ligature network similar to that previously described. However, in this embodiment, winder 128 only works with one end of band 124A, whose opposite end may either be anchored at another location or connected to another winder. Moreover, band 124A is not routed in a closed circuit in this embodiment.

An alternate guide 132A is shown as a cloth strip stitched into a loop that holds annular implement 133. Band 124A is shown routed through implement 133. Cloth loop 132A may be attached atop a padded shell by hook and loop fastening means, snaps, mechanical clips, etc.

Figure 9:
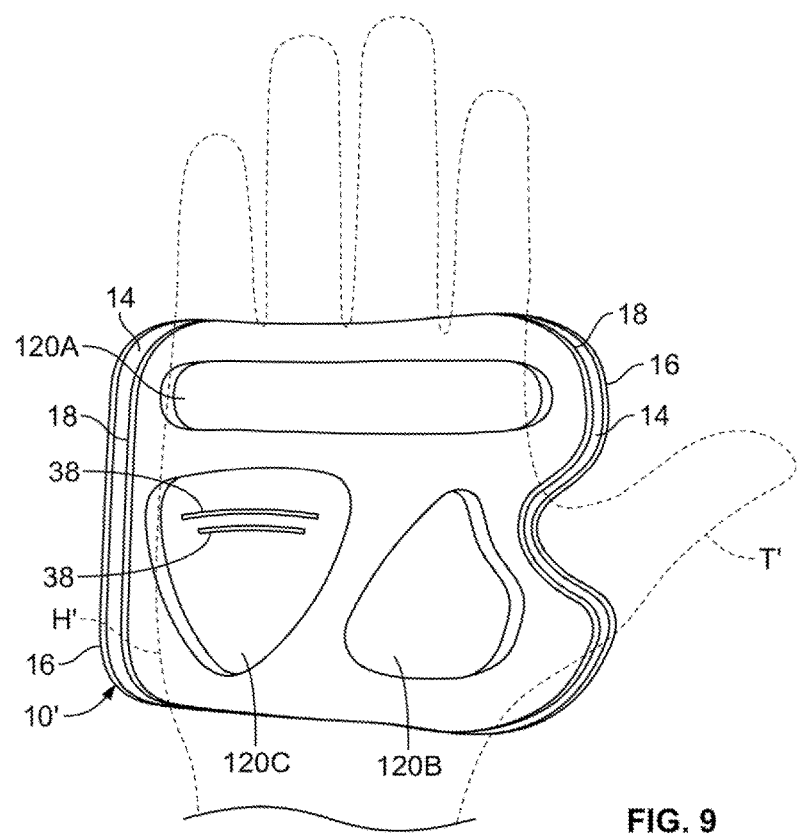
FIG. 9 is an inside view of a padded shell that is an alternate to that shown in FIG. 2.

Referring to FIG. 9, palmar shell 10' is designed for left hand H' and is substantially the mirror image of shell 10 of FIG. 2. As before, shell 10' has a heat deformable plastic core 14 with the same covering 16 and 18 as mentioned previously. In this embodiment, the layer 20 previously mentioned in FIG. 4 has been replaced with three disjoint segments 120A, 120B and 120C (also referred to as discrete panels). While three segments are shown, in other embodiments a greater or lesser number may be employed instead.

Segment 120A is an elongated slab with rounded ends designed to engage the knuckles of hand H'. Segment 120B has a teardrop shaped outline and is designed to engage the fleshy part of the palm at the base of thumb T'. Segment 120C is shaped to treat most of the remaining area of the palm of hand H' and has an outline that is roughly a triangle with rounded corners. Segment 120C is given some flexibility to bend along one of its edges by a pair of grooves 38.

It will be appreciated that the chosen outline, placement, thickness, and materials of segments 120A-120C will be tailored by the therapist that sets up the device, these choices being made to accommodate and best treat hand H'. Also, each of the discrete segments 120A-120C may be formed from the same material as layer 20 of FIG. 4, but in some cases each of the segments may use a different material with different characteristics adapted to accommodate the hand H' under treatment.

Panel segments 120A-120C may be overlaid (face to face) with a full panel (not shown) having an outline substantially the same as that of core panel 14 and made of material similar to panel 22 of FIG. 4. In other embodiments the roles may be reversed with the layer adjacent to the skin tissue being segmented, and the other layer being continuous.

Figure 10:
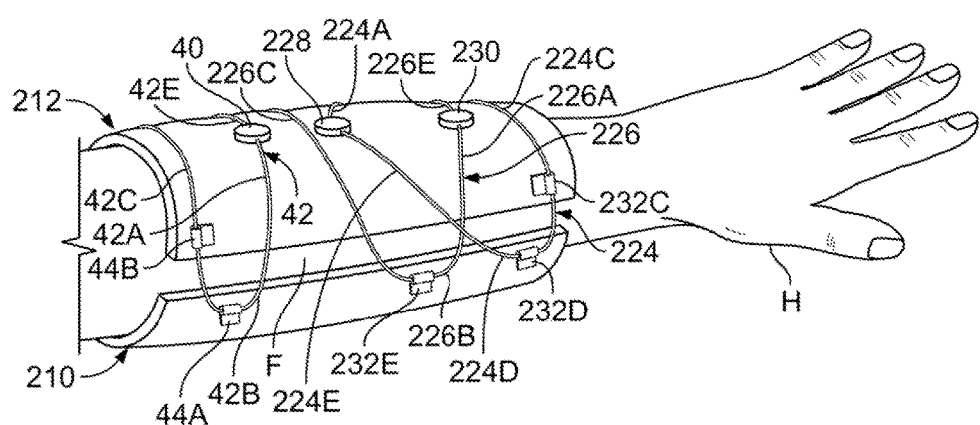
FIG. 10 is a perspective view of a compression device that is an alternate to that shown in FIGS. 1-3.

Referring to FIG. 10, the illustrated compression device is designed to treat a different body part, namely forearm F instead of hand H. Components in this Figure corresponding to those of the embodiment of FIGS. 1-7 have the same reference numerals but increased by 200. Padded shell 212 is shown on the extension side of forearm F and padded shell 210 is shown on the volar side of the forearm. Shells 210 and 212 are roughly semicylindrical and are layered in substantially the same manner as shown in FIG. 4.

Mounted on shell 212 are winders 230 and 228, which each have independently adjustable circuits 224 and 226, respectively. Winder 228 is shown connected to cord segments 224A and 224E of circuit 224. Winder 230 is shown connected to cord segments 226A and 226E of circuit 226.

Circuit 224 extends along cord segment 224E on shell 212, crossing over to shell 210 to form cord segment 224D, which passes through guide 232D before returning to shell 212 to form the cord segment 224C, passing through guide 232C. Cord segment 224C will pass through another guide (not shown) before taking a looping turn on a guide (not shown) on shell 210, eventually returning as cord segment 224A. It will be appreciated that circuit 224 has topographically the same routing as circuit 24 of FIGS. 1 and 2.

Circuit 226 is topographically the same as circuit 26 of FIGS. 1 and 2. Specifically, cord segment 226A crosses from shell 212 to shell 210 where cord segment 226B passes through guide 232E on shell 210 before returning to shell 212 to form cord segment 226C. Cord segment 226C will make a looping turn on a guide (not shown) on shell 210 before returning as cord segment 226E. It will be appreciated that circuit 226 has topographically the same routing as circuit 26 of FIGS. 1 and 2.

A third winder 40 on shell 212 connects to a third independently adjustable circuit 42 at cord segments 42A and 42E. Circuit 42 cooperates with a pair of guides at the proximal corner of shell 212, one such guide being shown as guide 44B. Guide 44A is mounted along the edge of shell 210 and a corresponding guide (not shown) is mounted at the opposite edge of shell 210 at the same longitudinal position.

Cord segment 42A extends across shell 212, crossing over to shell 210 where cord segment 42B passes through guide 44A before returning to shell 212 to form cord segment 42C, which passes through guide 44B and the complementary guide on the other side of shell 212. It will be appreciated that cord segment 42C crosses over to shell 210 and loops back in a manner similar to that shown for cord segment 42B.

As before, winders 228, 230 and 40 are releasably secured to shell 212 to allow a therapist to adjust the position of each. Similarly positionable are the guides (e.g., illustrated guides 232C-232E and 44A-44B).

Figure 11:
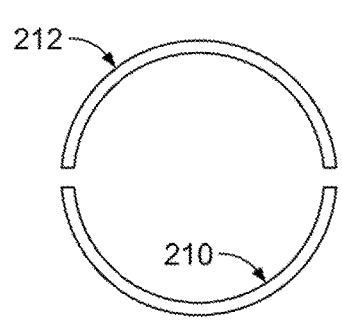
FIG. 11 is an end view of the device of FIG. 10.

As shown in FIG. 11, previously mentioned padded shells 210 and 212 have gaps at approximately the three o'clock and nine o'clock positions. In other embodiments such as shown in FIG. 12 three shells 46, 48, and 50 may be arranged with gaps at approximately the two o'clock, six o'clock and 10 o'clock positions (i.e., shell 46 on the extension side and shells 48 and 50 primarily on the volar side).

Figure 12:
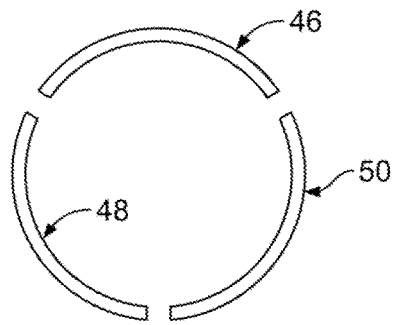
FIG. 12 is an end view of a device that is an alternate to that of FIG. 11.

While the devices of FIGS. 10-12 are mentioned for treating a forearm, they can equally be applied to different body parts such as the upper arm, calf, or thigh.

To facilitate an understanding of the principles associated with the foregoing apparatus, its operation will be briefly described in connection with the embodiment of FIGS. 1-7.

Heat deformable panel 14 is trimmed to size based on the size and proportions of hand H. To customize padded shell 12, hand H may be placed atop panel 14, palm up, and the outline of the hand may be traced with a pencil or other writing instrument. Panel 14 will then be trimmed to extend longitudinally from the end of the wrist to the base of the fingers. Panel 14 will also be trimmed to extend from the right to the left edge of the hand H with a little excess to allow the panel to curl slightly around the edge of the hand. Panel 14 will be allowed to extend outwardly slightly outwardly along extension 12A to cover a portion of the thumb knuckle. This extension will be useful in applying pressure in this region without restricting the mobility of thumb T.

To customize padded shell 10, hand H may be placed atop panel 14, palm down, and the outline of the hand may be traced with a pencil or other writing instrument. Panel 14 will be trimmed as before except that previously mentioned thumb extension 12A will be replaced with a thumb notch 10A. This notch will be useful in allowing articulation of thumb T. In fact, the wrist, thumb T and all the fingers of hand H can be moved so the user will retain most of the function of hand H. This ability to move the wrist and fingers and thereby exercise the hand will enhance the natural ability of the body to reduce edema by means of the natural pumping action produced when exercising the fingers and wrist.

Panels 14 of shells 10 and 12 can be further shaped by immersion in hot water to soften the panels. The panels may be curved in a general way to accommodate the shape of hand H. Special attention may be given to the right and left edges of panel 14 to roll these edges slightly around the hand H. For thumb extension 12A, panel 14 may be bowed about the thumb axis to provide a proper fit.

The foregoing trimming and shaping may be performed after a session with a therapist who examines and measures hand H. The therapist may either personally perform the trimming and shaping, but in some cases the information gathered by the therapist will be sent to a specialized lab along with a general description of the characteristics of hand H, so that the lab can customize the panel 14. In any event, this trimming and shaping will be based upon a therapist's experience and judgment.

Pads 20 and 22 (FIG. 4) may be provided as a kit having a variety of padding materials. The materials will offer a selection of different thicknesses, softness, etc. As noted above, the padding materials can include commercially available, closed cell foams that are designed for the treatment of lymphedema. The padding materials can also include softer, open cell foams of various types. In some cases the padding will be some other type of non-foam, synthetic material.

As noted previously, the padding may be cut into discrete segments as shown in FIG. 9. Again, the selection and arrangement of padding materials will be based on the therapist's experience and judgment.

Pad 20 may be secured in place by taking advantage of a natural propensity to adhere to hook and loop material 18. Where such a propensity does not exist, a mating sheet of a hook and loop material may be glued to pad 20. Likewise, hook and loop material may be used to connect pads 20 and 22 together. The advantage of using hook and loop material is that the therapist can experiment with a variety of combinations of pads and pad shapes. This ability to modify will be important when initially establishing the most desirable combination and also afterward when the arrangement needs to be modified as the patient's condition changes.

Also, while hook and loop fastening material will work satisfactorily, in some embodiments other fastening means may be employed, including releasable adhesives that allow repositioning and replacement of pads.

Next, a therapist will make judgments about the zones where pressure ought to be applied. In the embodiment of FIGS. 1-7, two compression zones are achieved by using two tensioners 28 and 30 and two independent circuits 24 and 26. A therapist can determine the course of circuits 24 and 26 by positioning guides 34 and 32A-32E. In the disclosed embodiment, circuit 24 is arranged with four crossovers between shells 10 and 12, which determine the compression forces between the shells.

For circuit 24, the compression affects primarily the knuckles at the base of the fingers. Specifically, the crossover between courses 24A and 24B applies pressure on the proximal and outer side of the knuckle for forefinger I. The crossover between courses 24B and 24C applies pressure on the distal side of the knuckles for fingers I and M, at the gap between those fingers. The crossover between courses 24C and 24D applies pressure on the distal side of the knuckles for fingers A and S, at the gap between those fingers. The crossover between courses 24D and 24E applies pressure on the distal and outer side of the knuckles for finger S.

For circuit 26, compression affects the portion of the hand H spaced proximally from the knuckles. Specifically, the crossover between courses 26A and 26B applies pressure on the pinky side of the hand about midway between the fingers and wrist. The crossover between courses 26B and 26C applies pressure on the pinky side of the hand at a position that is fairly close to the wrist. The crossover between courses 26C and 26D applies pressure on the thumb side of the hand between the thumb T and wrist. The crossover between courses 26D and 26E applies pressure on the thumb side of the hand about midway between thumb, T and forefinger I.

It will be appreciated that therapist can adjust the routing of courses 24 and 26 to change the manner in which pressure is applied to hand H. Also, since panels 14 of shells 10 and 12 are relatively stiff, the forces applied by the shells are substantially perpendicular to the palmar and dorsal surfaces of hand H, so that the hand is not squeezed laterally.

Winders 28 and 30 can be independently adjusted to establish the compression forces and their respective regions. By tightening (loosening) circuit 24 compression forces can be increased (reduced) around the knuckles at the base of the fingers. By tightening (loosening) circuit 26 compression forces can be increased (reduced) around the portion of hand H between the wrist and the knuckles at the base of the fingers. Normal forces will be transmitted primarily by pad 20. Pad 22 will usually be a softer material to increase comfort and to provide feathering of compression forces near the edges of shells 10 and 12.

Initially, the compression forces will be the established at the time the therapist first places the device on hand H. However, the patient will be taught how to independently place the device on hand H without professional assistance. Thereafter, the patient can wear the device during the time periods recommended by the therapist. In some cases, a patient may be asked to wear a compression glove under the device in order to assist in reducing edema, but this choice will depend upon the specific condition of this patient.

To don the device, one will start with winders 28 and 30 arranged to fully slacken circuits 24 and 26. A patient can then slip the fingers between shells 10 and 12 on the proximal edge of the shells. When hand H is positioned as shown in FIGS. 1-3, winders 28 and 23 can be adjusted to produce the tension in circuits 24 and 26 recommended by a therapist.

During the course of a day, a patient may find it necessary to increase or decrease the compression forces. Since winders 28 and 30 are easily adjusted, these compression forces can be easily changed. Also, the patient can be given a supply of replacement pads in order to replace pad 22 when it becomes soiled.

Also, the device is easily removed by using winders 28 and 30 to remove all tension on circuits 24 and 26. Thereafter, hand H is withdrawn in a direction opposite to the direction used to don the device. Accordingly, the patient can temporarily remove the device for routine activities such as bathing.

When the device is worn, the compression forces will tend to reduce the edema. The compression forces will tend to urge edematous fluids in a proximal direction. Also, the patient's fingers and thumb will remain highly mobile. Thus, the patient can perform most daily activities. Accordingly, the fingers and thumb will be routinely exercising, which will produce a natural pumping effect that tends to reduce edema. In addition, the device is relatively open so that air can reach the hand H, which will enhance comfort and avoid elevated temperatures.

The patient will still need to periodically visit a therapist to check the progress and to perform different types of CDT. At these visits the therapist can inspect the condition of the body part. If necessary, therapist can change pads 20 and 22 to a different type of pad.

The advantages of this device are: time savings and ease of application, comfort, safety, and therapeutic efficacy. Using appropriate materials and an effective tensioning system, this device offers a high working, low resting pressure environment similar to that which his offered to lymphedema patients during CDT using short stretch (non-elastic) bandaging materials. Furthermore compression is achieved while avoiding trauma to the lymphatic, hemodynamic and neurological system, by using customizable thermoplastics and padding to areas like the hand, forearm, upper arm, calf, thigh and other body parts.

It will be appreciated that various modifications may be implemented with respect to the above described embodiments. In some cases a variety of shells may be manufactured in sizes and shapes designed to accommodate the affected body part of most patients. In some embodiments shells may be provided with a large number of molded eyes or lacing hooks, so that the therapist can effectively route a tensioning cord through almost any desired route by selecting different eyes or hooks. In still other embodiments, the winders may be mounted in fixed positions, in which case the ligature network is adjusted by changing the routing of the cords connected to the tensioner. In some cases the ligature network will be formed of a single cord but will be segregated into different independent sections by tying some intermediate point on the cord to an anchor, so that tension is not transferred from one section to the other. While a double layer pad is disclosed, in some embodiments the pad may be a single layer or may employ more than two layers.

Obviously, many modifications and variations of the present invention are possible in light of the above teachings. It is therefore to be understood that within the scope of the appended claims, the invention may be practiced otherwise than as specifically described.

The invention claimed is:

1. A compression device for treating edema along a predetermined length and girth of a body part having a given contour, comprising:
    a mutually separated plurality of curved shells for encompassing the body part, each of said plurality of shells having an internal pad and a panel that is external to and stiffer than said internal pad, the stiffer panels of the mutually separated plurality of curved shells being arranged to encompass and confine the body part, each of said plurality of shells being adjacent to at least another one of said plurality of shells, each of said plurality of shells having a plurality of distinct edges, each adjacent pair of said plurality of shells being separated by a non-overlapping gap that is adapted to leave a portion of said body part uncovered by said plurality of shells and their internal pads; and
    a ligature network routed across said plurality of shells, and atop said plurality of shells, said ligature network being divided into a plurality of independently adjustable circuits, said network including:
    a plurality of tensioners directly attached to the panel of at least some of said plurality of shells, said plurality of tensioners being operable to separately adjust tension in different ones of said plurality of independently adjustable circuits to produce between said plurality of shells a pressure having a gradient for driving fluid in the body part in a desired direction, each of the independently adjustable circuits having separate portions that depart from an associated one of the plurality of tensionsers on an associated one of the plurality of shells to reach a separated pair of the plurality of distinct edges on the associated one of the plurality of shells, the separate portions adapted to be routed on the associated one of the plurality of shells in different directions relative to the girth of the body part, the separated pair of the plurality of distinct edges of the associated one of the plurality of shells facing away from each other, said plurality of tensioners contributing, compression forces perpendicular to the panels of the plurality of shells in order to apply compression forces between the panels along the length and girth of said body part, said panel having a stiffness that restricts flexing that is predominantly controlled by the contour of the body part, in order to avoid disparately redistributing compression force around the girth of said body part as tension changes in said plurality of circuits, the associated one of said plurality of tensioners being operable by increasing tension in one of said plurality of independently adjustable circuits to decrease the gap between the associated one of said plurality of shells and each of the plurality of shells adjacent to the separated pair of the plurality of distinct edges.

2. A compression device according to claim 1 said ligature network comprising:
    a plurality of guides attached to the panel of at least some of said plurality of shells, said guides being arranged to provide routing constraints for said ligature network.

3. A compression device according to claim 2 wherein said ligature network includes a cord, said plurality of guides comprising:
    at least one annular implement encircling said cord.

4. A compression device according to claim 3 wherein said plurality of guides comprises:
    at least one curved channel for turning said cord.

5. A compression device according to claim 1 wherein said ligature network includes a cord, said plurality of tensioners comprising:
    a manually operable winder for winding said cord.

6. A compression device according to claim 5 wherein said ligature network includes a tube encompassing a portion of said cord for reducing sliding friction on said cord.

7. A compression device according to claim 1 wherein said plurality of curved shells are heat deformable and curved to accommodate a body part of a patient.

8. A compression device according to claim 7 wherein said plurality of curved shells are perforated.

9. A compression device according to claim 1 wherein said pad comprises a pair of resilient layers.

10. A compression device according to claim 9 wherein said pair of resilient layers comprise:
    a closed cell foam panel; and
    an open cell foam panel lying face to face with said closed cell foam panel.

11. A compression device according to claim 9 wherein said pair of resilient layers for at least one of said plurality of shells comprise:
    a full panel; and
    a plurality of discrete panels each lying face to face with said full panel.

12. A compression device according to claim 1 wherein said plurality of tensioners are (a) releasably mounted on at least some of said plurality of shells, and (b) repositionable to allow spatial adjustment of compression forces produced by said compression device.

13. A compression device according to claim 12 wherein each of said tensioners comprises:
    a fastening device adapted to releasably attach to one of said plurality of curved shells.

14. A compression device according to claim 12 wherein at least one of said plurality of curved shells includes a covering of hook and loop material, at least one of said tensioners comprising:
    a sheet adapted to releasably attach to said covering of hook and loop material.

15. A compression device according to claim 12 wherein said ligature network comprises:
    a plurality of guides mounted on at least some of said plurality of shells, said guides being arranged to provide routing constraints for said ligature network.

16. A compression device according to claim 15 wherein each of said plurality of guides comprises:
a fastening member adapted to releasably attach to one of said plurality of curved shells.

17. A compression device according to claim 16 wherein at least one of said plurality of curved shells comprises:
a covering of hook and loop material, at least one of said tensioners including a sheet adapted to releasably attach to said covering of hook and loop material.

18. A compression device for treating edema along a predetermined length and girth of a body part, comprising:
a mutually separated plurality of curved shells, each having a plurality of distinct edges, and each having an internal pad and a panel that is external to and stiffer than said internal pad, the stiffer panels of the mutually separated plurality of curved shells being arranged to encompass and confine the body part, each of said plurality of shells being, adjacent to at least another one of said plurality of shells, each adjacent pair of said plurality of shells being separated by a non-overlapping gap that is adapted to leave a portion of said body part uncovered by said plurality of shells and their internal pads; and
a ligature network routed across said plurality of shells, said ligature network being divided into a plurality of independently adjustable circuits, said ligature network including:
a plurality of tensioners directly attached to the panel of at least some of said plurality of shells, at least a portion of said ligature network being releasably mounted and repositionable on said shells to allow spatial adjustment of compression forces produced by said compression device, each of the independently adjustable circuits having separate portions that depart from an associated one of the plurality of tensioners on an associated one of the plurality of shells to reach a separated pair of the plurality of distinct edges on the associated one of the plurality of shells, the separate portions adapted to be routed on the associated one of the plurality of shells in different directions relative to the girth of the body part, the separated pair of the plurality of distinct edges of the associated one of the plurality of shells facing away from each other, said plurality of tensioners contributing compression forces perpendicular to the panels of the plurality of shells in order to apply compression forces between the panels along the length and girth of said body part, the associated one of said plurality of tensioners being operable by increasing tension in one of said plurality of independently adjustable circuits to decrease the gap between the associated one of said plurality of shells and each of the plurality of shells adjacent to the separated pair of the plurality of distinct edges.

19. A compression device according to claim 18 wherein each of said tensioners comprises:
a fastening device adapted to releasably attach to one of said plurality of curved shells.

20. A compression device according to claim 18 wherein at least one of said plurality of curved shells includes a covering of hook and loop material, at least one of said tensioners comprising:
a sheet adapted to releasably attach to said covering of hook and loop material.

21. A compression device according to claim 18 wherein said ligature network comprises:
a plurality of guides mounted on at least some of said plurality of shells, said guides being arranged to provide routing constraints for said ligature network.

22. A compression device according to claim 21 wherein each of said plurality of guides comprises:
a fastening member adapted to releasably attach to one of said plurality of curved shells to allow repositioning thereon.

23. A compression device according to claim 22 wherein at least one of said plurality of curved shells comprises:
a covering of hook and loop material, at least one of said tensioners including a sheet adapted to releasably attach to said covering of hook and loop material.

24. A compression device according to claim 22 wherein said ligature network includes a cord, said plurality of guides comprising:
at least one annular implement encircling said cord.

25. A compression device according to claim 22 wherein said plurality of guides comprises:
a curved channel for turning said cord.

26. A compression device according to claim 18 wherein said ligature network includes a cord, said tensioner comprising:
a manually operable winder for winding said cord.

27. A method for treating edema with a ligature network and a mutually separated plurality of curved padded shells, each having a plurality of distinct edges, and each having an internal pad and a stiffer external panel, comprising the steps of:
routing the ligature network in a plurality of independently adjustable circuits across the plurality of shells with the network directly anchored at one or more points of the stiffer external panel of one or more of the plurality of padded shells; and
with a length and girth of a body part embraced by the padded shells and the padded shells mutually separated, and with the stiffer panels of the mutually separated plurality of curved shells being arranged to encompass and confine the body part, separately adjusting tension in different portions of said ligature network to peripherally urge together the plurality of padded shells by applying compression forces between the panels along the length and girth of said body part in order to (a) affect the balance of compression forces at spaced positions along said plurality of padded shells in order to drive fluid in the body part in a proximal direction, and (b) simultaneously maintain a non-overlapping gap between each adjacent one of the plurality of padded shells, the non-overlapping gap overlying a portion of said body part that remains uncovered by the plurality of padded shells, tension being applied through the ligature network directly to the stiffer panel of at least some of the padded shells at a location where nearby portions of the ligature network have been routed to depart from an associated one of the plurality of shells to reach a separated pair of the plurality of distinct edges on the associated one of the plurality of shells, the nearby portions being routed on the associated one of the plurality of shells in different directions relative to the girth of the body part, the separated pair of the plurality of distinct edges of the associated one of the plurality of shells being positioned to face away from each other, tension in one of the plurality of independently adjustable circuits being increased to decrease the gap between the associated one of the plurality of shells and each of the plurality of shells adjacent to the separated pair of the plurality of distinct edges.

28. A method according to claim 27 comprising the step of:
adjusting the routing of the ligature network to adjust the balance of compression forces at spaced positions along said plurality of padded shells.

29. A method according to claim 28 wherein said ligature network employs a plurality of network tensioners and a plurality of network guides on at least one of said padded shells, wherein the step of adjusting the routing of the ligature network is performed by:
adjusting the position of said network tensioners and network guides.

30. A method according to claim 27 wherein the ligature network, includes at least one cord, the step of separately adjusting tension includes the step of:
winding the cord to adjust its tension.

31. A method according to claim 27 wherein the step of routing the ligature network is performed by:
configuring the ligature network into a plurality of independently adjustable circuits.

32. A method according to claim 31 comprising the step of:
trimming the outline of at least some of the plurality of padded shells to accommodate the body part of an individual patient.

33. A method according to claim 32 comprising the step of:
customizing the curvature of the plurality of padded shells to accommodate the body part of an individual patient.

34. A method according to claim 31 wherein at least one of said padded shells has a pad with a number of disjoint segments, the method comprising the step of:
trimming the disjoint segments of the pad to accommodate the body part of an individual patient; and
placing the disjoint segments alongside each other on the padded shell.

35. A method according to claim 31 wherein at least one of said padded shells has a pad, the method comprising the step of:
cutting grooves in the pad in a pattern to accommodate the body part of an individual patient.

36. A method according to claim 27 comprising the step of:
bandaging the body part to compress the body part over the course of multiple days before using the padded shells.

37. A method according to claim 36 comprising the step of:
temporarily removing the padded shells from the body part for a period of time every day during a course of treatment.

38. A method for treating edema with a ligature network and a mutually separated plurality of curved padded shells, each having a plurality of distinct edges, and each having an internal pad and a stiffer external panel, comprising the steps of:
adjusting routing of said ligature network across the plurality of shells to provide tailored compression forces at spaced positions along said plurality of padded shells while keeping the ligature network directly anchored at one or more points of the stiffer external panel of one or more of the plurality of padded shells; and
with a length and girth of a body part embraced by the padded shells and the shells mutually separated, and with the stiffer panels of the mutually separated plurality of curved shells being arranged to encompass and confine the body part, adjusting tension in said ligature network to (a) adjust compression forces along said plurality of padded shells by applying compression forces between the panels along the length and girth of said body part in order to drive fluid in the body part in a proximal direction, and (b) simultaneously maintain a non-overlapping gap between each adjacent one of the plurality of padded shells, the non-overlapping gap overlying a portion of the body part that remains uncovered by the plurality of padded shells, tension being applied through the ligature network directly to the stiffer panel of at least some of the padded shells at a location where nearby portions of the ligature network have been routed to depart from an associated one of the plurality of shells to reach a separated pair of the plurality of distinct edges on the associated one of the plurality of shells, the nearby portions being routed on the associated one of the plurality of shells in different directions relative to the girth of the body part, the separated pair of the plurality of distinct edges of the associated one of the plurality shells being positioned to face away from each other, tension in one the plurality of independently adjustable circuits being increased to decrease the gap between the associated one the plurality of shells and each of the plurality of shells adjacent to the separated pair of the plurality of distinct edges.

* * * * *